United States Patent [19]

Gainer, Jr.

[11] 4,070,460
[45] Jan. 24, 1978

[54] METHOD FOR TREATING CEREBRAL EDEMA

[75] Inventor: James V. Gainer, Jr., Kingwood, W. Va.

[73] Assignee: University of Virginia Patents Foundation, Charlottesville, Va.

[21] Appl. No.: 630,684

[22] Filed: Nov. 10, 1975

[51] Int. Cl.$^2$ ............... A61K 31/70; A61K 31/23; A61K 31/19; A61K 31/20
[52] U.S. Cl. ............... 424/180; 424/312; 424/317; 424/318; 424/325; 424/343
[58] Field of Search ............ 424/318, 180, 312, 317, 424/343, 325

[56] References Cited

U.S. PATENT DOCUMENTS

| 3,788,468 | 1/1974 | Gainer | 424/318 |
| 3,853,993 | 10/1974 | Gainer | 424/180 |

OTHER PUBLICATIONS

The Merck Index, Eighth edition, 1968, Merck & Co., Inc., Rahway, N.J., pp. 294 & 486.

*Primary Examiner*—Frederick E. Waddell
*Attorney, Agent, or Firm*—Oblon, Fisher, Spivak, McClelland & Maier

[57] ABSTRACT

A method for the treatment of cerebral edema in mammals which comprises administering to said affected mammal an effective dose of a water soluble carotenoid.

5 Claims, No Drawings

METHOD FOR TREATING CEREBRAL EDEMA

BACKGROUND OF THE INVENTION

1. Field of the Invention

This invention relates to a novel technique for the treatment of cerebral edema in mammals.

2. Description of the Prior Art

In U.S. Pat. Nos. 3,853,992 and 3,788,468, it is disclosed that certain water-soluble carotenoids had been observed to possess quite unique properties. In particular, these water-soluble carotenoids have been found to increase the diffusivity of oxygen through aqueous media. The effect was found further to be useful biologically in the treatment of atherosclerosis, which had been theorized as being a disease resulting from local hypoxia of the vascular walls.

The study of the biological effects of this compound has continued with the present discovery that it has effectiveness in the treatment of cerebral edema.

Cerebral edema is a condition characterized by an abnormal accumulation of fluid within the brain tissue. In general two main types have been differentiated, i.e,. extracellular vasogenic edema and intracellular edema induced by cytotoxic factors. In vasogenic edema, fluid leaks out of the capillary into the extracellular space. The major area of fluid accumulation is in the extracellular space in the white matter.

Heretofore dexamethasone has been used for the treatment of cerebral edema, with fair results. Although no mechanism has been established to explain why this drug is effective, it was theorized that its effectiveness was somehow related to its apparent ability to reduce capillary permeability.

DETAILED DESCRIPTION OF THE PREFERRED EMBODIMENTS

The present inventor began his study of cerebral edema with an investigation of the mechanism to explain the effectiveness of dexamethasone, which was formerly used for the treatment of this disorder. The investigations of the present inventor seem to show, that dexamethasone increases the ability of the plasma to hold dissolved oxygen. This would result in a net increase of available oxygen to the capillary wall.

Since it has been found that certain carotenoid compounds, especially crocetin, cause an increase in the diffusion rate of oxygen, it was then theorized that this mechanism might produce a net increase in available oxygen to the capillary wall by a different mechanism and cause a reduction in cerebral edema.

This theory was tested and determined to be correct by empirical investigation.

The carotenoids useful for this purpose are those of the form:

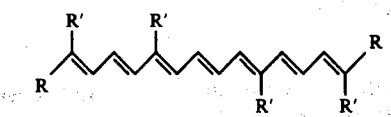

wherein each R may represent a hydrophilic group and each R' represents hydrogen or methyl. Suitable hydrophilic groups include the carboxyl groups or the ester groups of the form COOR" wherein R" represents a soluble sugar group, such as $C_{12}H_{21}O_{10}$, an alkanol group, such as $-CH_2-OH$, $-CH_2-CH_2-OH$, or $-CH_2-CH_2-OH$, or a carboxy substituted lower alkyl, such as $-CH_2-COOH$, $-CH_2-CH_2COOH$ or $-CH_2-CH_2-CH_2COOH$, or each R and R' may represent a lower alkanol group, such as $-CH_2-OH$, $-CH_2-CH_2-OH$, or $-CH_2-CH_2CH_2-OH$, a hydroxy group, or an amine group of the form $-NH$ or $NR'''$ wherein $R'''$ is a lower alkyl, lower alkanol or carboxy substituted lower alkyl, or a carboxy substituted lower alkyl, such as $-CH_2-CH_2-OH$, $-CH_2-OH$, or $-CH_2-CH_2-CH_2-OH$.

Most preferred are crocetin, also known as 8, 8'-diapo-8,8'- carotenoic acid, or crocin, also known as digentiobiosyl 8,8'-diapo-8,8'- carotenedioate, or a salt, such as the sodium salt, or crocetin.

The water soluble carotenoids have been found to be effective in the treatment of cerebral edema when applied either by injection intramuscularly or intravenously into the animal. They could also be given orally.

The carotenoid can be injected into the patient, and in an injectable form, it may be combined with vitamins, choline, glycerophosphoric acid, glycol, glycerine or gum tragacanth, etc.

The animal or human is treated with from 0.001 to 1000 mg of active ingredient per kg of body weight each application, for a total weekly dose rate of 0.001 to 1000 mg of active ingredient per kg of body weight/day, and preferably, from 0.005 to 500 mg/kg/day or 0.001 to 1000 mg/kg/week.

The effectiveness of the water soluble carotenoids has been indicated by tests with mongrel cats, which are the standard test animals often used for experimental treatment techniques of this disorder (see I.Klatzo, et al. The Relationship between Edema, Blood Brain Barrier and Tissue Elements in Local Brain Injury, Journal of Neuropathology & Experimental Neurology 17:548-564, 1958; H. Pappius, Effects of Steroids on Cold Injury Edema Steroids & Brain Edema, Reulen et al, editors, N.Y. Heidelberg, Berlin, Springer-Verlag 1972 pp. 57-63).

Having generally described the invention, a more complete understanding can be obtained by reference to certain specific examples, which are included for purposes of illustration only and are not intended to be limiting unless otherwise specified.

EXAMPLES

In the testing of the pharmaceutical for efficacy, over 57 cats, each averaging 2-4 kg., were tested. The method for determining edema used in these experiments is outlined in Rouit et al: Steroids & Cerebral Edema; Journal of Neuropathology 27:277-299 (1968). The animals were anesthetized with ketamine, and a right parietal craniotomy done with removal of a 15 mm diameter circle of bone. The dura was opened and a freezing lesion made on the cortex with a modified Cooper cryosurgical probe cooled to $-50°$ C. The cortical lesion diameter was 10 mm. The bone was replaced and the scalp closed. The animals were then sacrificed at periods of 24or 48 hours after the production of the lesion. Representative sections were taken through the area of the lesion in the right hemisphere, and sections through a comparable area in the left hemisphere were taken for comparison. Wet weights were determined. Percentage water loss could then be determined, and by comparing the lesion side with the non-lesion side in the same animal the increase in edema in the area of lesion could be determined.

Also, Evans Blue dye was injected into the animals intravenously prior to producing the lesion. This dye leaks out of the capillaries in the area of edema, and provides a means of visually outlining the area of edema. Measurements of the area of dye extravasation were made as a further means of determining the area and amount of edema in the lesion side.

Groups of animals were done using no drugs (control groups), using crocetin injected before making the lesion or afterward, using dexamethasone both before and after the lesion, and using both dexamethasone and crocetin after the lesion.

Crocetin was given to the pre-treated cats as follows: 150 micrograms intramuscularly twice daily, beginning 2 days prior to the lesion and continuing until sacrifice.

Crocetin was given to the post-treated cats as follows: 150 micrograms intravenously 30 minutes after production of lesion, and 150 micrograms intramuscularly 6 hours later. After that 150 micrograms was given intramuscularly twice daily until sacrifice.

Dexamethasone was given in a dosage calculated to produce a plasma level of 3-4 micrograms per cc of plasma. Four times the calculated dose was given as a loading dose intravenously and the calculated dose given intramuscularly every 6 hours thereafter until sacrifice.

A pretreated group was given dexamethasone intramuscularly every 6 hours for 24 hours prior to making the lesion. The drug was continued every 6 hours after making the lesion until sacrifice at 24 or 48 hours. A post-treated group was started on dexamethasone 30 minutes after the lesion was made and continued every 6 hours until sacrifice at 24 or 48 hours.

The results are summarized in Table 1.

TABLE I.

WHITE MATTER EDEMA

A. Sacrifice at 24 Hours

| Group | Number of Cats | Edema (Gm/Gm of Brain Tissue) | Percent Changes | Significance (P) | Dye Extravasation (Sq. Cm.) | Percent Changes | Significance (P) |
|---|---|---|---|---|---|---|---|
| Control | 11 | .081 | — | — | 1.63 | — | — |
| Crocetin (Pre-Treated) | 4 | .016 | −80 | .025 | 1.02 | −37 | .07 |
| Dexamethasone (Pre-Treated) | 4 | .041 | −49 | .15 | .96 | −41 | .05 |
| Crocetin (Post-Treated) | 4 | .045 | −44 | .15 | 1.01 | −38 | .05 |
| Dexamethasone (Post-Treated) | 4 | .052 | −36 | .2 | 1.08 | −34 | .07 |
| Dexamethasone and Crocetin (Post-Treated) | 4 | .045 | −44 | .2 | .79 | −52 | .05 |

B. Sacrifice at 48 Hours

| Group | Number of Cats | Edema (Gm/Gm of Brain tissue) | Percent Changes | Significance (P) | Dye Extravasation (Sq. Cm.) | Percent Changes | Significance (P) |
|---|---|---|---|---|---|---|---|
| Control | 4 | .096 | — | — | 1.88 | — | — |
| Crocetin (Pre-Treated) | 6 | .013 | −86 | .005 | .46 | −76 | .001 |
| Dexamethasone (Pre-Treated) | 4 | .065 | −32 | .2 | 1.03 | −45 | .001 |
| Crocetin (Post-Treated) | 4 | .052 | −48 | .05 | .91 | −52 | .01 |
| Dexamethasone (Post-Treated) | 4 | .076 | −21 | .3 | 1.04 | −45 | .05 |
| Dexamethasone and Crocetin (Post-Treated) | 4 | .045 | −58 | .05 | .62 | −67 | .01 |

At 24 hours, both dexamethasone and crocetin produced a reduction in edema percentage-wise. Pretreatment of the animals with crocetin resulted in a significant 80% reduction of edema formation. The post-treated animals had a 44% reduction of edema, and this was significant to the 0.15 level. With dexamethasone, pretreatment resulted in an edema reduction of 49% and post-treatment in 36% reduction. At 48 hours, crocetin produced a reduction of edema of 82% in the pre-treated animals and 48% in the animals started on treatment after production of the lesion. These values . are statistically significant. Dexamethasone produced a 32% reduction in edema at 48 hours in the pretreated animals and 21% in the post-treated ones. Significant reduction of dye extravasation occurred in both the crocetin and dexamethasone groups at 24 and 48 hours, with the crocetin groups having slightly better results. No significant effect was produced on gray matter edema with crocetin or dexamethasone.

As noted previously, it has been established that the water soluble carotenoids, and in particular crocetin, will increase the diffusion speed of oxygen through plasma. This mechanism should result in a net increase in the available oxygen at the capillary endothelial level. We have postulated that oxygen availability at this level is a critical factor in the development of vasogenic edema, and an increase in oxygen availability to the capillary cell will tend to decrease vasogenic edema. Our results from this study would tend to indicate that this is true. Treatment with these compounds was significantly effective in reducing edema.

Whether the effect is primarily due to free radical scavenging by oxygen or due to providing a means of increasing the metabolic rate of the capillary cells and hastening repair is not certain. Probably both effects occur.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A method for the treatment of cerebral edema which comprises administering to an affected mammal an effective dose of a water-soluble carotenoid.

2. The method of claim 1, wherein said water-soluble carotenoid has the formula

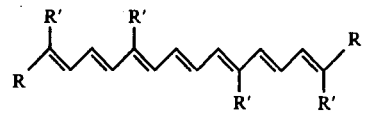

wherein each R is a hydrophilic group, and wherein each R' is hydrogen or methyl.

3. The method of claim 1, wherein said water-soluble carotenoid is crocin.

4. The method of claim 1, wherein said water-soluble carotenoid is crocetin.

5. The method of claim 1, wherein said water-soluble carotenoid is administered intravenously or intramuscularly at a dose rate of from 0.001 mg to 1000 mg active ingredient per gk of body weight per week.

* * * * *